United States Patent
Waszak et al.

(10) Patent No.: US 10,222,255 B2
(45) Date of Patent: Mar. 5, 2019

(54) MEASUREMENT HEAD FOR A LINEARLY OVERLAPPING LIGHT MEASUREMENT SYSTEM

(71) Applicants: John P Waszak, Westford, MA (US); Stephen J Waszak, Escondido, CA (US)

(72) Inventors: John P Waszak, Westford, MA (US); Stephen J Waszak, Escondido, CA (US)

( * ) Notice: Subject to any disclaimer, the term of this patent is extended or adjusted under 35 U.S.C. 154(b) by 61 days.

(21) Appl. No.: 15/678,288

(22) Filed: Aug. 16, 2017

(65) Prior Publication Data

US 2018/0073919 A1    Mar. 15, 2018

Related U.S. Application Data

(60) Provisional application No. 62/385,964, filed on Sep. 10, 2016.

(51) Int. Cl.

| | |
|---|---|
| *G01J 1/04* | (2006.01) |
| *G01J 1/42* | (2006.01) |
| *G01J 1/32* | (2006.01) |
| *G01J 3/10* | (2006.01) |
| *G01N 21/88* | (2006.01) |
| *G01J 3/50* | (2006.01) |

(52) U.S. Cl.
CPC ............... *G01J 1/0403* (2013.01); *G01J 1/32* (2013.01); *G01J 1/4228* (2013.01); *G01J 3/10* (2013.01); *G01N 21/8806* (2013.01); *G01J 3/501* (2013.01)

(58) Field of Classification Search
CPC .... G01J 1/0403; G01J 1/32; G01J 3/10; G01J 1/4228; G01J 3/501; G01N 21/8806

USPC ................................................ 250/559.29
See application file for complete search history.

(56) References Cited

U.S. PATENT DOCUMENTS

| | | | | |
|---|---|---|---|---|
| 6,038,028 A | * | 3/2000 | Grann | G01B 11/0691 356/630 |
| 8,049,892 B2 | * | 11/2011 | Shakespeare | G01J 3/36 356/402 |

* cited by examiner

*Primary Examiner* — Seung C Sohn

(57) ABSTRACT

A linearly-overlapping light measurement system "measurement head" having one or more linearly-overlapping modular light sources each having individual light sources arranged in a geometric pattern, the light sources being single- or multi-wavelength and programmable to generate light that is transmitted through and/or reflected from a work piece to be detected by linearly-overlapping modular light detectors having individual light detectors arranged in a geometric pattern. The "measurement head" also has linearly-overlapping modular light detectors arranged in a geometric pattern to receive light emitted by the light sources. A computer controller coordinating the operation of the light source array and light detector array to automatically sense and record the light transmittance and/or reflectance of one or more spectral ranges in real time from the work piece and then adjust the work being performed on the work piece to attain pre-determined standards. Reference feedback circuitry is provided for monitoring the light sources in each light source module. The reference feedback circuitry adjusts the operating parameters of a light source module to ensure that the intensity and the chromatic output of the light therefrom remains at a consistent level.

15 Claims, 7 Drawing Sheets

MEASUREMENT HEAD FOR A LINEARLY OVERLAPPING LIGHT MEASUREMENT SYSTEM

RELATED APPLICATIONS

This application claims the benefit of U.S. Provisional Application 62/385,964 filed Sep. 10, 2016 which is incorporated herein in its entirety by reference.

FIELD OF THE INVENTION

This invention relates to the use of optical measurement techniques to control the quality and consistency of an environment or, more commonly, a manufactured product. A common use of such techniques applies to the printing or converting industries where the consistency of color is measured using optical techniques including optical transmittance, optical reflectance, and optical density (a base 10 logarithmic scale applicable to both transmittance and reflectance). The same techniques apply to any product manufacturing that benefits from the consistency of the optical qualities themselves, or the physical properties that can be inferred from the optical properties, for example coating thickness or resistivity. The device detailed herein is optimized for continuous linear monitoring across a material's width, such information which can be aggregated over time to create a two-dimensional mapping of single- or multi-spectrum optical properties over the entire width and length of a product while it is being manufactured.

BACKGROUND OF THE INVENTION

The prior art, as exemplified in U.S. Pat. Nos. 7,626,724, 5,073,028, 4,003,660, and 3,995,958, provides methods and apparatus to measure light for the purpose of monitoring light transmittance through a work product and light reflectance from a work product. This prior art utilizes a moving platform to exhaustively sample a linear segment of a work product, as well as expensive detector filtering and/or light dispersion The prior art, as exemplified by U.S. Pat. No. 6,671,052 describes a static, multi-point densitometer with between 1 and 8 sensors per probe for monitoring and quality control of work product by measuring the transmissive or reflective optical density. Adjustments are then determined and made to achieve the desired optical density value.

The prior art does not teach, and there is a need, for a light measurement system head ("measurement head") having elongated, modular, interlocking modules, each module having a linearly-overlapping orientation of a plurality of light sources or light detectors. Multiple light source modules are interlocked together and multiple light detector modules are interlocked together into a chosen length and used to exhaustively map a linear segment of a work product of a given width passing lengthwise beneath the interlocked light source modules and the interlocked light detector modules.

The prior art also does not suggest or teach, and there is a need, utilizing an onboard light source reference function to maintain consistent light intensity output from the light source modules of the "measurement head".

The prior art also does not suggest or teach, and there is a need, for a peripheral temperature function to monitor and control for temperature impacts on both the light source modules and light detector modules.

Thus, there is a need in the prior art for an improved light measurement system "measurement head" for monitoring the transmittance of light through a work product or the reflectance of light from a work product that meets the above described need in the prior art. This improved light measurement system "measurement head" provides an end to end interlocking design of a plurality of light source modules and an end to end interlocking design of a like plurality of light detector modules. This permits a linearly-overlapping orientation across multiple modules that can be used to exhaustively map a linear segment of a work product of a given width passing lengthwise beneath the interlocked light source modules and the interlocked light detector modules. There is an onboard light source reference function to maintain consistent light intensity output from the light source modules, and a peripheral temperature function to monitor and control temperature impacts on both the light source modules and light detector modules.

SUMMARY OF THE INVENTION

The aforementioned needs in the prior art are met by the present invention which is an improved light measurement system "measurement head" for monitoring either the transmittance of light through a work product or the reflectance of light from a work product. This improved light measurement system "measurement head" provides an end to end interlocking design of a plurality of light source modules and an end to end interlocking design of a like plurality of light detector modules the. This permits a linearly-overlapping orientation across multiple modules that can be used to exhaustively map a linear segment of a work product of a given width passing lengthwise beneath the interlocked light source modules and the interlocked light detector modules. There is an onboard light source reference function that helps maintain consistent light intensity output from the individual light sources of each light source module, and there is also a peripheral temperature function to monitor and control temperature impacts on the operation of both the light source modules and light detector modules.

The "measurement head" of the invention is summarized in a linearly-overlapping arrangement of light sources that can either project light through a medium or material of a work product in a transmissive manner with the resulting light levels being incident on a linearly-overlapping arrangement of light detectors, or it can reflect light from a medium or material of a work product in a reflective manner with the reflected light being incident on a linearly overlapping arrangement of light detectors.

The linearly overlapping arrangement of light sources of the "measurement head" produces a light pattern whose detection width is greater than the pitch between any two linearly adjacent detectors. As a result, the width of a work product is exhaustively sampled in real time, without any moving parts that would increase serviceability time due to calibration requirements and wear. The interlocking design allows any number of linearly-overlapping light sources and light detectors to be physically combined, creating any length of exhaustively mapped linear segments.

In the case that the individual light sources within a light detector module contain multiple spectra of light, for example multiple LED lighting elements mounted in each singular light source, the light sources can be independently programmed to produce any combination of spectra, each at a programmable intensity. With a broadband light detector, the intensity, transmittance, or reflectance of any single spectrum or combination of spectra can be monitored in real-time, continuously across a linear segment of a work product. This provides obvious applicability in color monitoring, as well as many other less obvious applications where the transmittance or reflectance of multiple ultraviolet, visible, and/or infrared spectral "bands" can be combined to infer other physical properties.

In the event that a light source intensity varies, an on-board reference circuit on the light source module of the "measurement head" can detect the change and report the change to the computer control mechanism via an API. The affected light source(s) can also make their own automated adjustments to their generated light level, thus creating a self-regulating light output.

In the event that the light levels incident upon the light detectors of the "measurement head" become too low, an intermediate gain stage, followed by an automatic gain control stage in a light detector, autonomously increases the gain, producing a seamless detection system capable of measuring over six decades of light intensity.

In this manner the invention exhaustively samples the transmittance and/or reflectance of a linear segment of a work product passing beneath light source modules and light detector modules of the "measurement head", using real-time sampling to map multiple linear segment samples over a two-dimensional space, so as to provide continuous inspection of a sheet or roll ("web") of the work product being manufactured with various coatings.

The invention provides this continuous linear monitoring without the need for any moving parts, thereby reducing the operating costs and downtime, both planned and unplanned, for the product lifecycle.

The purpose of the invention is to rapidly sample the entire linear segment such that a thorough mapping of a moving web of work product can be obtained, without the gaps in mapping inherent in prior art technologies that only scan across the width of a work product.

BRIEF DESCRIPTION OF THE DRAWINGS

The invention will be better understood upon reading the following Detail Description in conjunction with the drawing in which.

DETAILED DESCRIPTION

Figure 4:
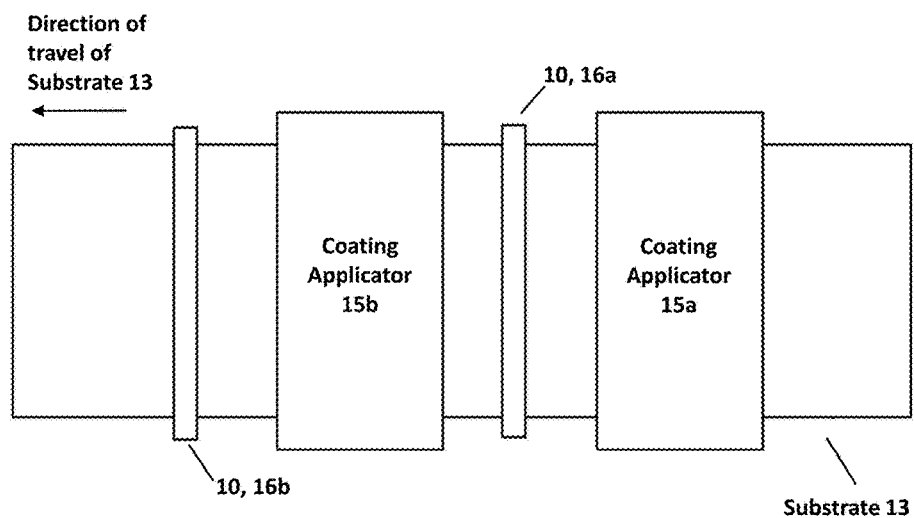
FIG. 4 is a top view diagram showing a plurality of light measurement system "measurement heads" being employed with two sequenced coating applications.

In summary, the invention is embodied in a light measurement system "measurement head" 10 that monitors the thickness of a coating being deposited on a sheet of material (hereinafter substrate 13 in the FIGS.) without the need for any moving parts. "Measurement head" 10 comprises one or more light source modules 11 and, typically, a like number of light detector modules 12 (FIGS. 1, 2 and 14) each having a plurality of components all arranged in a linearly-overlapping manner as shown (FIG. 4,5,6). In a light source module 11 (FIG. 5) there are two rows of light source units 11$a$ and 11$b$ with each individual light source unit having one or more wavelength variable light emitting diodes (11 $w,x,y$). In a light detector module 12 (FIG. 6) there are two rows of light detector units 12$a$ and 12$b$.

The light measurement system "measurement head" 10 has one or more linearly-overlapping modular light sources 11 having individual light sources 11$a$, 11$b$ arranged in a geometric pattern, the light sources being single- or multi-wavelength 11$w,x,y$ and programmable to generate light that is transmitted though and/or reflected from a work piece 13 to be detected by linearly-overlapping modular light detectors 12$a$, 12$b$ having individual light detectors arranged in a geometric pattern. A computer controller 17, 27 coordinates the operation of the light source modules and light detector modules to automatically sense and record the light transmittance and/or reflectance of one or more spectral ranges in real time from the work piece 13 and then adjust the work being performed on the work piece 13 to attain pre-determined standards.

This controls the quality and consistency of an environment or, more commonly, a manufactured product or work product 13. A common use of such a system applies to the printing or converting industries where the consistency of color is measured using optical techniques including optical transmittance, optical reflectance, and optical density (a base 10 logarithmic scale applicable to both transmittance and reflectance). The same techniques apply to any product manufacturing that benefits from the consistency of the optical qualities themselves, or the physical properties that can be inferred from the optical properties, for example coating thickness or resistivity. The "measurement head" 10 detailed herein is optimized for continuous linear monitoring across the width of a material 13. Such information which can be aggregated over time to create a two-dimensional mapping of single- or multi-spectrum optical properties over the entire width and length of a material while it is being manufactured.

Figure 7:
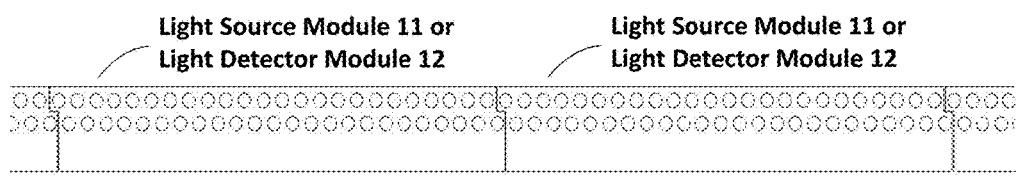
FIG. 7 shows the interlocking module design that allows a continuous, linearly overlapping lighting and detection area across multiple segments.

A number of light source modules 11 or a number of light detector modules 12, each mounted in an individual tray, may be mechanically connected in a serial manner to stretch across any width of material/substrate 13 as shown in FIG. 7. They are not intermixed. Only light source modules 11 are connected to light source modules 11 and light detector modules 12 are connected to light detector modules 12 in order to function properly. This may be done in a light transmittance mode of operation with the light detector modules 12 being on an opposite side of the substrate 13 from the light source modules 11 (eg FIGS. 1&2). Alternatively, this may be done in a light reflective mode of operation with the light detector modules 12 being on the same side of the substrate 13 from the light source modules 11 as shown in FIG. 3. In the light reflective mode the light source array modules 11 and the light detector modules 12 are located on the same side of the substrate 13, at one or more predetermined angles relative to each other. In both configurations, a computer control, via a high-level API, configures each light source unit within each light source module 11 with a given intensity. In cases where each light source unit 11$a$ or 11$b$ has multiple light source elements (eg 11$w,x,y$), the computer control has the option of setting the intensity of each individual light detector element 11$w,x,y$ in each light detector unit 11$a$ or 11$b$, including selectively shutting off one or more of the elements. Intensity can be controlled by means of adjusting the current powering each light source element and/or the pulse width of a frequency generator powering the elements 11$w,x,y$.

Figure 5:
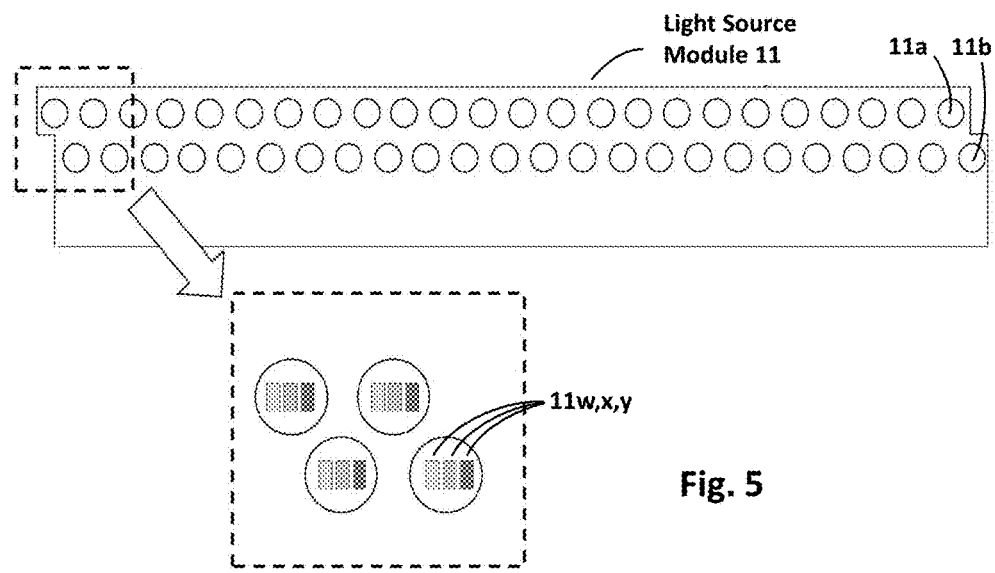
FIG. 5 depicts the plurality of individual LED's 11$w,x,y$ grouped within each of the linearly-overlapping light sources.
Figure 6:
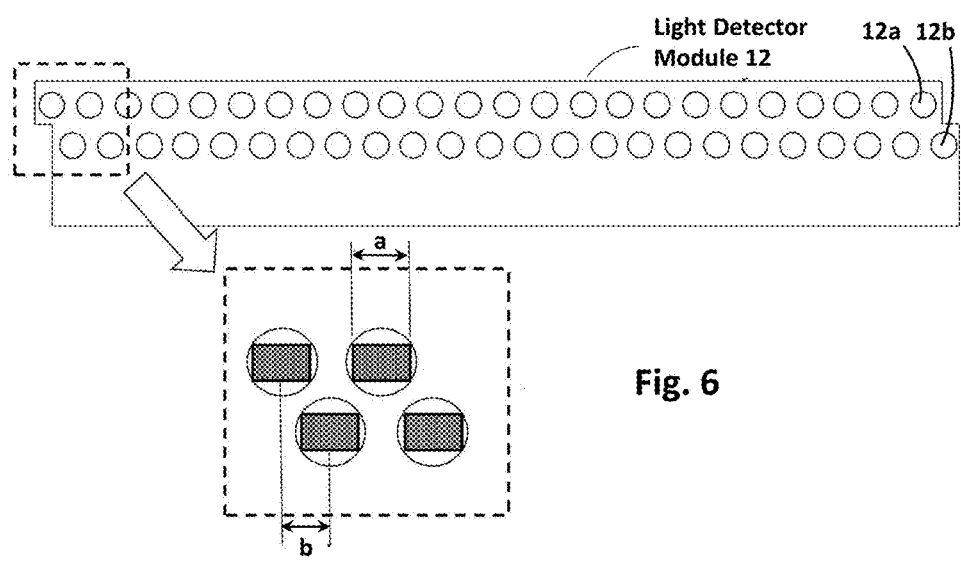
FIG. 6 depicts the overlapping geometry of a light detector module 12. The center-to-center spacing, "b", is less than the width of the active area, "a", producing an overlapping sensing area among detector elements.

A staggered orientation of the light sources units 11$a$ or 11$b$ in accordance with the teaching of the invention is shown in FIG. 5. This includes grouping of multiple light elements 11$w,x,y$ within each light source 11$a$ or 11$b$. In FIG. 6 is shown the staggered orientation of the light detectors 12, including the linearly-overlapping orientation of the detector's active surface area.

Figure 1:
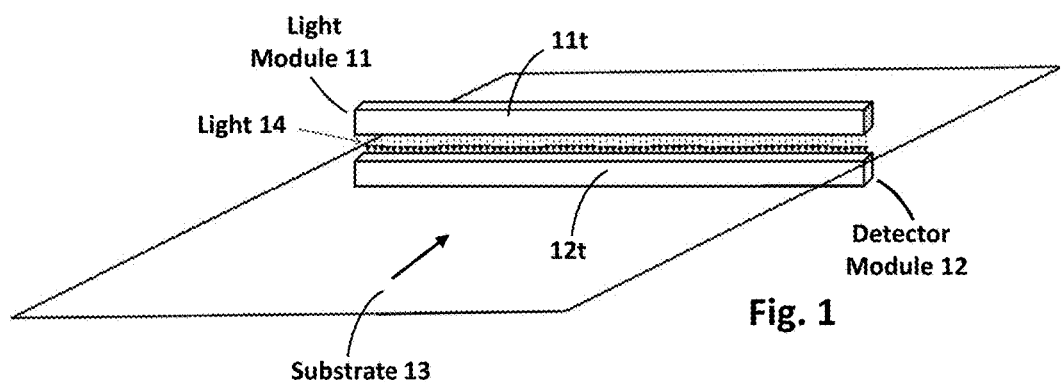
FIG. 1 is a three-dimensional view of the novel light measurement system "measurement head" operating in a transmissive mode measuring the optical properties a sheet of material/substrate passing between a linearly overlapping light source module and a linearly overlapping light detector module.

FIG. 1 is a three-dimensional view of the light measurement system "measurement head" 10 operating in a transmissive mode measuring the optical properties a sheet of substrate 13 passing between a linearly overlapping light source module 11 and a linearly overlapping light detector module 12. Module 11 has a plurality of LED light source units 11$a,b$ in two rows each source having multiple light elements 11$w,x,y$ (see FIG. 5). Each of the plurality of LED light sources in FIG. 1 is shown transmitting in a downward direction as represented by the small arrowheads through substrate 13 in a transmissive mode of operation. The amount of light 14 from each LED light source unit 11$a,b$ that impinges on the corresponding light detector 12$a,b$ below it depends on the transmissive properties of a coating that has been deposited on the surface of substrate 13 (not shown) or through just substrate 13. Each light source module 11 is mounted in a tray 11$t$ that is attached to a framework that is not shown. Each light detector module 12 is also mounted in a tray 12$t$ that is attached to a framework that is not shown. Multiple trays are mechanically linked together to form one virtually continuous tray.

Figure 2:
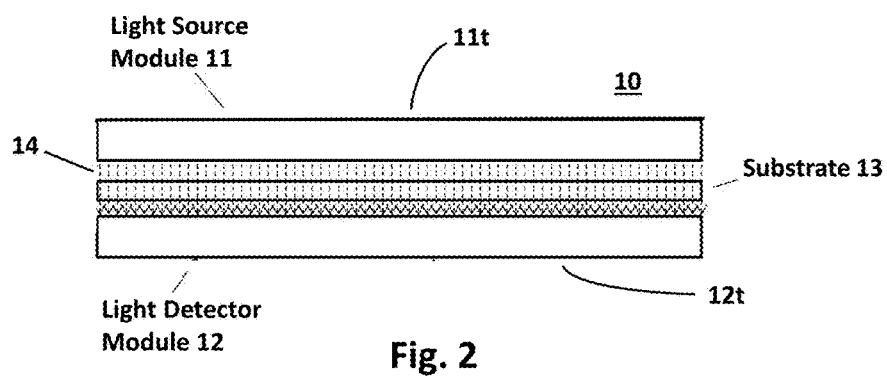
FIG. 2 is a diagram showing a typical front edge view of the novel light measurement system "measurement head" operating in a transmissive manner measuring optical properties of a sheet of material/substrate passing between a linearly overlapping light source array module and a linearly overlapping light detector array module.
Figure 3:
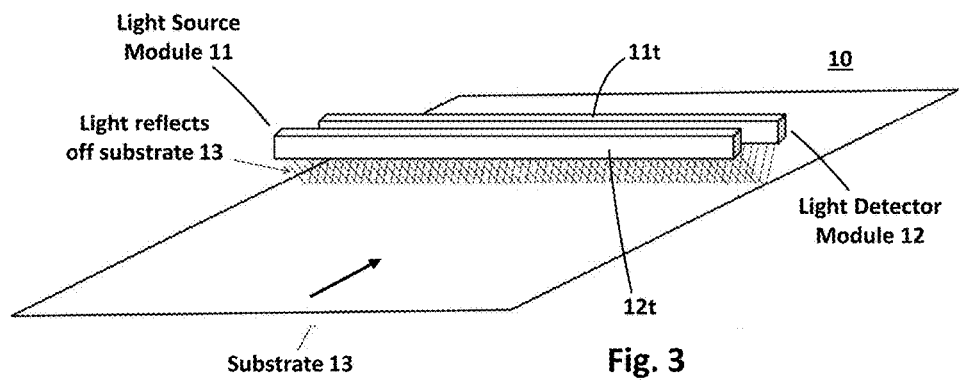
FIG. 3 is a three-dimensional view of the light measurement system "measurement head" operating in a reflectance mode and measuring the optical properties of a sheet of coated material/substrate passing beneath both linearly overlapping light source modules and linearly overlapping light detector modules.

FIG. 2 is a diagram showing a typical front edge view of the novel light measurement system "measurement head" 10 operating in a transmissive manner measuring optical properties of a sheet of material/substrate 13 passing between a linearly overlapping light source module 11 and a linearly overlapping light detector module 12. The amount of light 14 from each LED light source that impinges on the corresponding light detector below it depends on the transmissive properties of a coating that has been deposited on the surface of substrate 13 (not shown) or through just substrate 13. Module 11 is mounted in a tray 11$t$ that is attached to framework that is not shown. Module 12 is also mounted in a tray 12$t$ that is attached to framework that is not shown.

FIG. 3 is a three-dimensional view of the light measurement system "measurement head" 10 operating in a reflectance mode and measuring the optical properties of a sheet of coated material/substrate 13 passing beneath both linearly overlapping light source module 11 and linearly overlapping light detector module 12. It can be seen that light emitted by each light element 11$w,x,y$ of each light source unit 11$a$,1$b$ of light source module 11 reflects off the top surface of substrate 13 and impinges on the corresponding light detector 12$a,b$ adjacent to it.

FIG. 4 is a diagram showing a two-stage version of the light measurement system "measurement head" 16$a$, 16$b$ where the transmissive and/or reflective optical properties of a substrate 13 that has been coated by a first stage coating applicator 15$a$ are measured by a first stage 16$a$ of the light measurement system, and the measurement results are used to adjust the operation of a second stage coating applicator 15$b$ to achieve more accurate transmissive and/or reflective optical properties as measured by a second stage 16$b$ of the light measurement system. The first stage of the light measurement system 16$a$ is typically the same as the second stage of the light measurement system 16$b$, and each stage comprises a light source module 11 and light detector module 12 as shown in FIGS. 1 and 3. First coating applicator 15$a$ applies a first coating to substrate 13, the results of which are measured by the first light measurement system "measurement head" 10, 16$a$. The once coated substrate 13 will then pass through a second coating applicator 15$b$, which applies an additional coating formulation, the results of which are measured by the second light measurement system 10, 16$b$. The two measurements can be used to inspect the results of each coating application as well as in a differential mode to inspect the difference in optical response between coating applicators 15$a$ and 15$b$.

Figure 9:
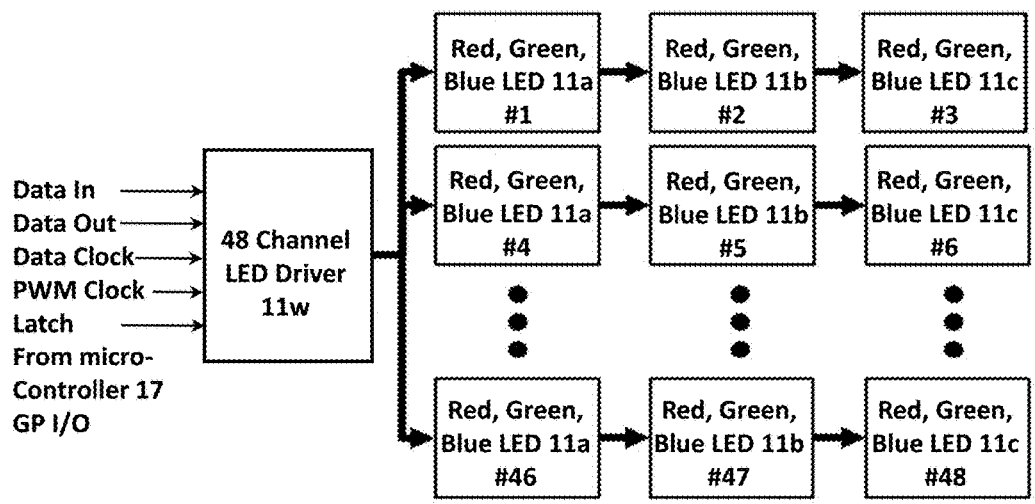
FIG. 9 is a block diagram schematic showing more detail of Precision LED Lighting Control 34 shown as a block in FIG. 8.

FIG. 5 is a diagram showing a light source array module 11 having two staggered rows 11$a$ and 11$b$ of light sources, represented as circles, creating a linearly-overlapping light pattern in accordance with the teaching of the invention. The spacing between light sources (shown as circles) in each of rows 11$a$ and 11$b$ is 8.3 millimeters, and the spacing between rows 11$a$ and 11$b$ is 16.7 millimeters. The LED light sources are available from L&M Instruments LLC, 1902 Wright Place, Cornerstone Corporate Center, Carlsbad, Calif. 92008-6583. A portion of the left end of module 11 is blown up and each light source unit in module 11 comprises LED light sources elements 11$w,x,y$ each generating a different wavelength of light. Three individual LED elements 11$w,x,y$ are shown in FIG. 5 and they are independently programmed to produce combinations of the light spectra, each at a given wavelength and programmable intensity. One or all of three LED light sources elements 11$w,x,y$ may be concurrently lit to generate a light output of a given wavelength and intensity. Each individual LED element 11$w,x,y$ is controlled via the 48 Channel LED Driver 11$s$ (FIG. 9). The individual LED elements of each light source unit can be simultaneously energized, each at a variable level of drive current, to create custom colors or spectral distributions, or they can be sequentially energized to produce separate spectrums across the time-domain. The individual LED's 11$w,x,y$ can be part of a pre-packaged LED, a Red-Green-Blue LED, or individually-packaged LED's. One, two, or three individually-packaged LED's can be employed.

To eliminate light crosstalk in light detector modules 12, illumination of adjacent light sources within a light source module 11 may be varied to eliminate optical cross-talk that may become incident in the corresponding light source detectors in module 12 of a "measurement head".

Light source elements 11$w,x,y$ in the light source units 11$a$ and 11$b$ of a module 11 may utilize less expensive LED light sources, as opposed to a more expensive and less robust light-dispersion technique using the light detectors 12.

Light source modules 11 are each mounted in a tray 11$t$ (not shown in detail) for use as shown in FIGS. 1, 2 and 3. The bottom of the tray 11$t$ has a plurality of electrical contacts. The bottom side of each light source module 11 has a like plurality of electrical contacts arranged in a mirrored pattern to the electrical contacts inside the bottom of tray 11$t$. Microprocessor controlled circuitry is connected to the electrical contacts inside the bottom of tray 11$t$ to control the light emitted by the light source module 11, and is connected to the electrical contacts inside the bottom of tray 12$t$ to process and utilize the light detected by the light detector modules 12.

FIG. 6 is a diagram showing a light detector array module 12 having two staggered rows of light detector units 12$a$ and 12$b$, creating a linearly-overlapping light detection pattern, and showing each individual light detector unit having multiple detector elements, where the width "a" of a light detector unit active sensing area is 9.91 millimeters and is greater than the pitch "b" between light detector units which is 8.3 millimeters. The spacing between light detectors (shown as circles) in each of rows 12$a$ and 13$b$ is 8.3 millimeters, and the spacing between rows 12$a$ and 12$b$ is 16.7 millimeters. The LED light detectors are available from L&M Instruments LLC, 1902 Wright Place, Cornerstone Corporate Center, Carlsbad, Calif. 92008-6583.

The invention also allows the ability to simultaneously monitor several wavelengths of light, either in a transmittance mode or a reflectance mode of operation, or concurrently in both modes of operation, to continuously inspect characteristics such as color, moisture absorption, or UVA and UVB transmittance, etc. When both modes of operation are being utilized, there may be a single light source module and two light detector modules, but there may also be two or more of each type of module.

With a broadband light detector 12, the intensity, transmittance, or reflectance of any single spectrum or combination of spectra can be monitored in real-time, continuously across a linear segment of a work product. This provides obvious applicability in color monitoring, as well as many other less obvious applications where the transmittance or reflectance of multiple ultraviolet, visible, and/or infrared spectral "bands" can be combined to infer other physical properties.

FIG. 7 is a diagram showing multiple modules (either light source modules 11 or light detector modules 12), the modules being mated together to form a longer, continuous arrangement of light sources 11 or light detectors 12. As previously described a plurality of light source modules 11, each in a tray 11$t$, may be mated together to illuminate the entire width of a substrate 11 passing below them. Similarly, a plurality of light detector modules 12, each in a tray 12$t$, may be mated to gather to concurrently detect all light passing through our being reflected from the entire width of the same substrate 13. This interlocking design is employed on both the printed-circuit assemblies that comprise the electronics as well as the structural housing around the electronics. Hidden pins in the sides of the housings, as well as structural top-covers that span the segments, provides rigidity.

As previously described with reference to FIGS. 1 and 2, the bottom of trays 11$t$ have a plurality of electrical contacts used to provide electrical connections to a light source modules 11 and the bottom of the trays 12$t$ have a plurality of electrical contacts used to provide electrical connections to a light detector modules 12. As described elsewhere herein, microprocessor controlled circuitry is connected to the electrical contacts inside the bottom of each of trays 11$t$ to control the light emitted by the light source module 11, and is connected to the electrical contacts inside the bottom of each of trays 12$t$ to process and utilize light detected by the light detector modules 12.

Figure 8:
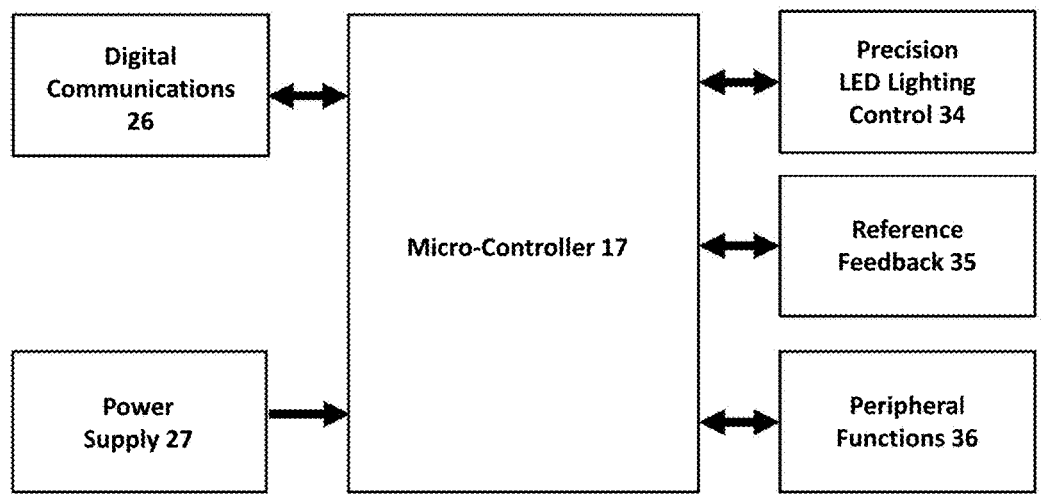
FIG. 8 is a block diagram of the core logic of a light source module 11.

FIG. 8 is a block schematic of a microprocessor and associated components of the novel light measurement system "measurement head". To further stabilize the operation of the invention real-time reference feedback 35 is provided to compensate for changes in the light source intensity, due to temperature or any other environmental, power, or aging conditions, as well as automation to produce highly consistent light output across all those conditions. The operating temperature of the light source elements in a light source module 11 are monitored and, using the temperature measurements, real-time reference feedback circuit 35 adjusts the operating parameters of the light source module 11 to ensure that the intensity and the chromatic output of light from the light source module 11 remain at a predetermined level.

FIG. 9 is a block diagram schematic of the electronics of each light source module for providing precision LED lighting control. The 48 Channel LED Driver 11$w$ takes typical inputs from Microcontroller 17 including a serial clock signal, serial data input and output signals, a pulse-width-modulated (PWM) clock signal to control brightness, and a chip-select signal utilizing a GP I/O. 48 Channel LED Driver 11$w$ then drives 48 outputs organized as 16 multi-LED strands, each strand with 3 individual LED outputs. Each of the 16-strands, in turn, drives a series of 3 multi-LED devices. While FIG. 9 depicts the multi-LED components as red, green, and blue, other wavelengths in the ultraviolet, visible, or infrared spectrum can be employed. Control of the LED's includes PWM ("grey-scale" control) and drive current control including color adjustment, brightness control, and dot correction. This provides a wide range of capability to control for discrepancies of individual LED characteristics resulting from the manufacturing process. Feedback from 48 Channel LED Driver 11$s$ to Microcontroller 17 also includes LED-shorts and LED-opens, to allow automated fault detection.

Figure 10:
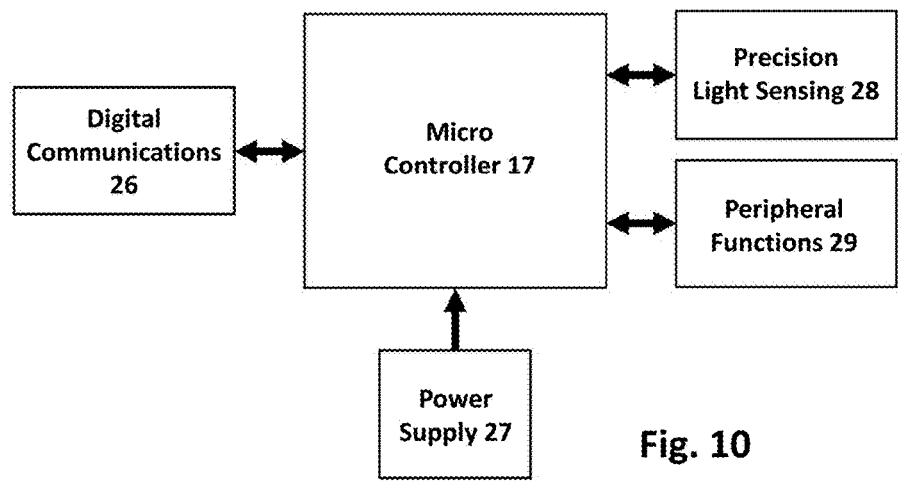
FIG. 10 is a block diagram schematic of the core logic comprising a light detector module 12.

FIG. 10 is an overall block diagram schematic of the microprocessor control of the light detector modules 11 of a "measurement head". Along with Digital Communications 26, Power Supply 27, and Peripheral Functions 29 described above, is Precision Light Sensing 28 which is further described with reference to FIG. 12. Photodiode Array 11 consists of 48 separate photodiodes. Each photodiode is connected to 48 individual trans-impedance amplifiers (Trans-impedance amp 24), converting the current output of the photodiode to a voltage. This voltage is, in turn, fed into three 16-channel analog multiplexers, Analog MUX (16:1) 30$a, b, c$. The multiplexer output is fed into an intermediate gain stage, with programmable gain. The signal is then further conditioned by an automatic gain stage, AGC Stage 32 a, b, and c. This arrangement provides a high dynamic range and low noise for 48 photodiodes.

Figure 11:
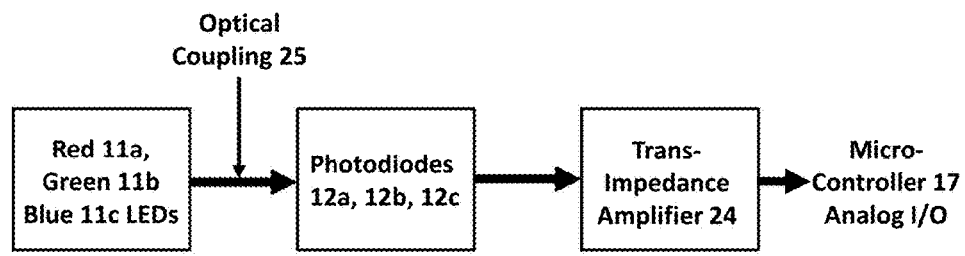
FIG. 11 is a block diagram schematic of the reference feedback circuitry for each light source in each light source module.

FIG. 11 is a block diagram schematic of the reference feedback circuitry for each light source in each light source module 11. It is this reference feedback circuitry 35 that adjusts the operating parameters of the light source module 11 to ensure that the intensity and the chromatic output of light from a light source module 11 remains at a predetermined level.

Figure 12:
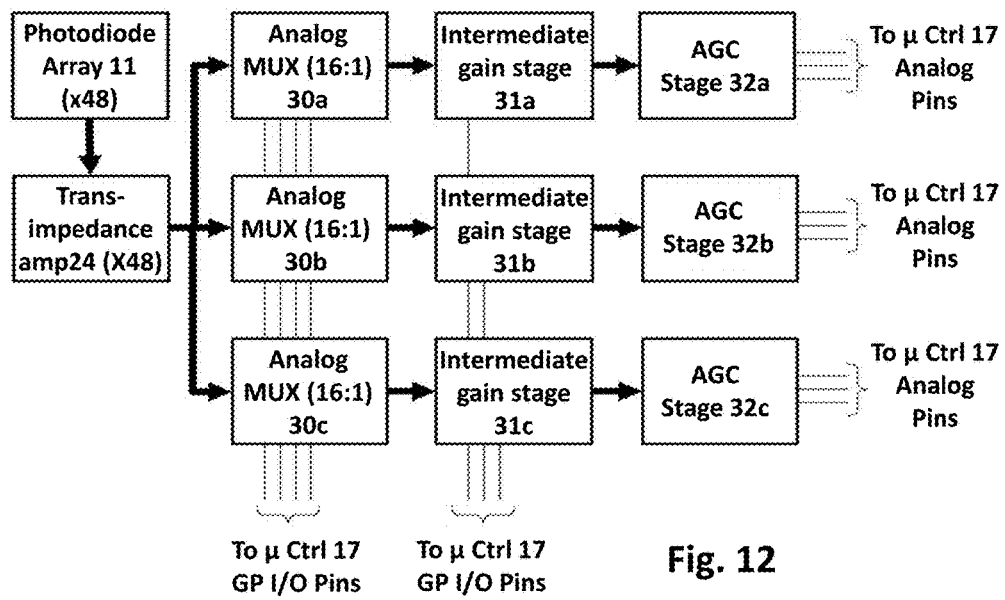
FIG. 12 is a block diagram schematic of a light detector module precision light-sensing function 28.

FIG. 12 is a block diagram schematic of a light detector modules 12 precision light-sensing function.

Figure 13:
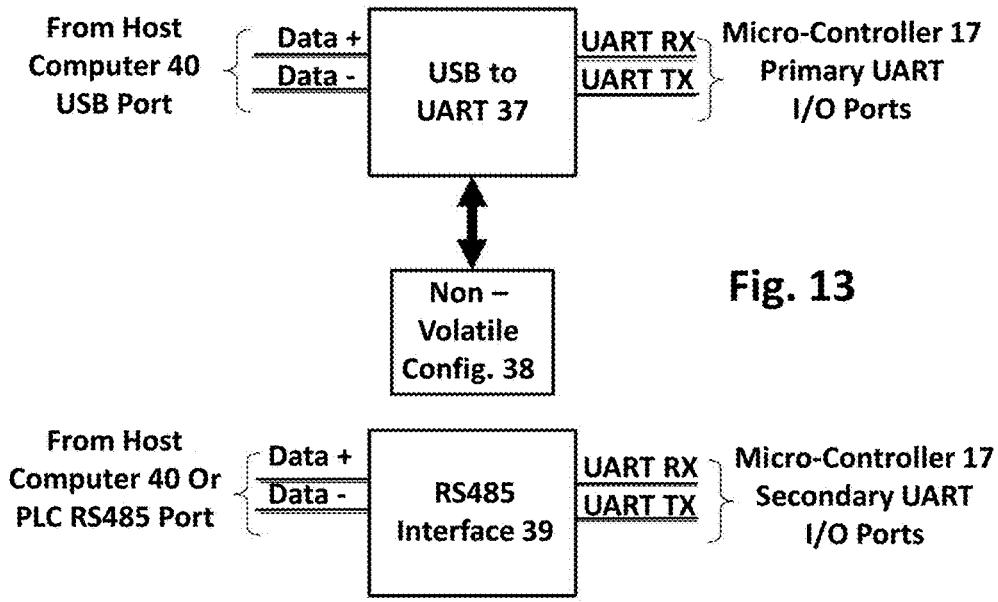
FIG. 13 is a block diagram schematic of the digital communications function of the novel light measurement system "measurement head" that functions with both the light source modules 11 and the light detector modules 12.

FIG. 13 is a block diagram schematic of the digital communications function of the novel light measurement system "measurement head" that functions with both the light source modules and the light detector modules. The invention provides flexible digital communications including the use of either USB or RS485 connectivity. The RS485 connectivity supports a "multi-drop" architecture whereby multiple light source arrays and light detector arrays can be accessed over a single 2-wire RS485 network.

Figure 14:
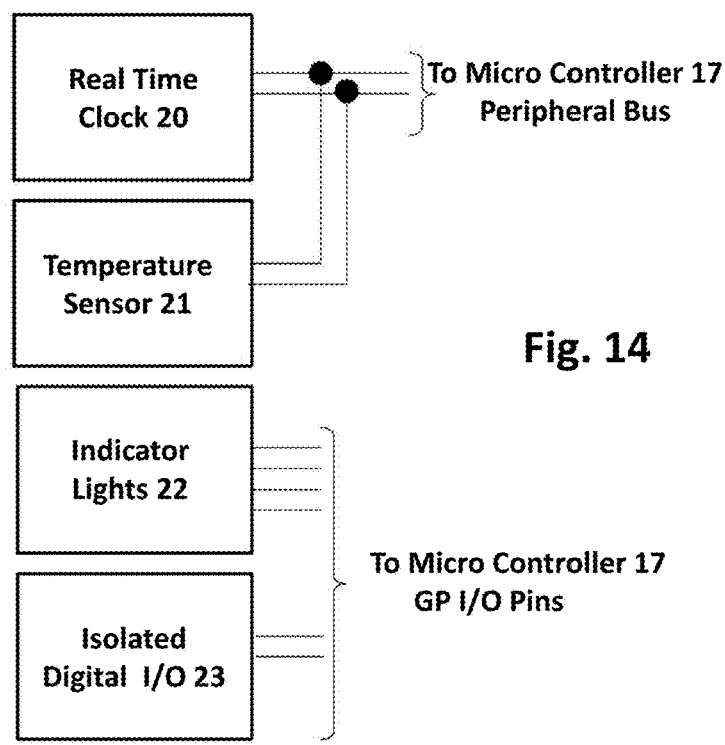
FIG. 14 is a block diagram schematic of the peripheral functions of both the light source modules 11 and the light detector modules 12.

FIG. 14 is a block diagram schematic of the peripheral functions of both the light source modules and the light detector modules. Indicator lights 12 are provided and used as visible indicators of health and status of the system 10. In addition, digitally isolated input and output pins are provided for other interfacing options in a production environment.

In an alternative embodiment of the light measurement system "measurement head" 10 shadowing mechanisms (not shown) are utilized to filter out extraneous ambient light, thereby eliminating the need for costly optical filters.

In another embodiment of the light measurement system "measurement head" 10 a light detector module 12 is used to provide a precision, linearly-overlapping light detector device to monitor the stability of existing light sources used for other purposes such as UV curing of materials.

In yet another embodiment of the light measurement system "measurement head" 10 a light detector module 12 may be used provide other spatial orientations of continuous lighting and light detection to exhaustively map the transmittance and/or reflectance properties of areas such as those produced by warning lights, vehicle head-lamps, etc.

In yet another embodiment of the light measurement system "measurement head" 10 a light source module 11 can be used to provide UV light for the disinfection of materials passing underneath, including surgical gloves, and detector module 12 may be used to ensure the light levels are within specification to produce the desired disinfection effect across a linearly-overlapping orientation. Light level feedback from module 12 can then be back to LED driver 11s of light source module 11 to regulate the light output.

While what has been described hereinabove is a preferred embodiment of the invention, it will be obvious to those skilled in the art that numerous changes may be made without departing from the spirit and scope of the invention.

What is claimed is:

1. A modular measurement head used in a light measurement system for measuring light transmitted through or reflected from a material, the measurement head having a controller for controlling the operation of the measurement head, the measurement head comprising:
　at least one light source module, the light source module consisting of a plurality of multi-wavelength, programmable, light source elements arranged in a geometric pattern that transmit light in a linearly overlapping manner with respect to each other, the transmitted light being reflected from or transmitted through the material in order to measure the properties of the material; and
　at least one light detector module, the light detector module consisting of a plurality of broadband light detector elements arranged in a geometric pattern alike the geometric pattern of the light source elements on the light source module to allow continuous, uninterrupted monitoring of the light reflected from or transmitted through the material from a corresponding light source module;
　wherein the controller coordinates the operation of the light source modules and the light detector modules so as to automatically sense and record the transmittance of the light through or reflectance of the light from the material in real time and to make adjustments accordingly.

2. The modular measurement head of claim 1 wherein the plurality of light source elements in the light source module are arranged in two staggered rows, creating the linearly overlapping geometric pattern, each light source comprising one or more wavelength variable light elements.

3. The modular measurement head of claim 2 wherein the plurality of light detector elements in the light detector module are arranged in two staggered rows, creating the linearly overlapping geometric pattern that allows continuous, uninterrupted monitoring of the light from a corresponding light source module to be reflected from or transmitted through the material.

4. The modular measurement head of claim 1 wherein there are a plurality of light source modules each having an interlocking edge design so as to permit multiple said light source modules to be physically and electrically mated together to form a continuously linearly overlapping segment of light source modules of varying length.

5. The modular measurement head of claim 4 wherein there are a plurality of light detector modules each having an interlocking edge design so as to permit multiple said light detector modules to be physically and electrically mated together to form a continuously linearly overlapping segment of light source modules of varying length.

6. The modular measurement head of claim 4 further comprising a first tray in which the plurality of light source modules are mounted to be physically and electrically mated together.

7. The modular measurement head of claim 5 further comprising a second tray in which the plurality of light detector modules are mounted to be physically and electrically mated together.

8. The modular measurement head of claim 1 further comprising means for measuring the operating temperature of the light source elements in a light source module and using the temperature measurements to adjust the operating parameters of the light source module to ensure that the intensity and the chromatic output of light from the light source module remain at a predetermined level.

9. The modular measurement head of claim 8 wherein there are a plurality of light source modules each having an interlocking edge design so as to permit multiple said light source modules to be physically and electrically mated together to form a continuously linearly overlapping segment of light source modules of varying length.

10. The modular measurement head of claim 9 wherein there are a plurality of light detector modules each having an interlocking edge design so as to permit multiple said light detector modules to be physically and electrically mated together to form a continuously linearly-overlapping segment of light source modules of varying length.

11. The modular measurement head of claim 10 further comprising a first tray in which the plurality of light source modules are mounted to be physically and electrically mated together.

12. The modular measurement head of claim 11 further comprising a second tray in which the plurality of light detector modules are mounted to be physically and electrically mated together.

13. The modular measurement head of claim 7 wherein the plurality of light detector elements in the light detector module are arranged in two staggered rows, creating the linearly overlapping geometric pattern.

14. The modular measurement head of claim 6 wherein the plurality of light source elements in a light source module are arranged in two staggered rows, creating the linearly overlapping geometric pattern that allows continuous, uninterrupted monitoring of the light from a corresponding light source module that is reflected from or transmitted through the material.

15. The modular measurement head of claim 1 wherein each light source module comprises an on-board reference control circuit that measures the operating temperature of the light source module and uses it to adjust the operating parameters of the on-board reference control circuit to ensure that the intensity and the chromatic output of light from the light source module remains constant.

\* \* \* \* \*